United States Patent
Williams et al.

(10) Patent No.: US 6,174,540 B1
(45) Date of Patent: Jan. 16, 2001

(54) LONG ACTING INJECTABLE FORMULATIONS CONTAINING HYDROGENATED CASTER OIL

(75) Inventors: James B. Williams, Lansdale; Rey T. Chern, Harleysville, both of PA (US)

(73) Assignees: Merck & Co., Inc., Rahway; Merial LLC, Iselin, both of NJ (US)

( * ) Notice: Under 35 U.S.C. 154(b), the term of this patent shall be extended for 0 days.

(21) Appl. No.: 09/152,775

(22) Filed: Sep. 14, 1998

Related U.S. Application Data

(60) Provisional application No. 60/067,374, filed on Dec. 3, 1997.

(51) Int. Cl.[7] .................................................. A61F 2/02
(52) U.S. Cl. ............................................... 424/423
(58) Field of Search ............................................... 424/423

(56) References Cited

U.S. PATENT DOCUMENTS

| | | |
|---|---|---|
| 4,181,721 | 1/1980 | Speck et al. . |
| 4,330,538 | 5/1982 | Itil et al. . |

FOREIGN PATENT DOCUMENTS

| | | |
|---|---|---|
| 196 13 972 | 10/1997 | (DE) . |
| 0 413 538 | 2/1991 | (EP) . |
| 0 535 734 | 4/1993 | (EP) . |
| 1060632 | 3/1967 | (GB) . |
| WO 97-11709 | 4/1997 | (WO) . |

*Primary Examiner*—Carlos A. Azpuru
(74) *Attorney, Agent, or Firm*—Shu M. Lee; Mollie M. Yang; David L. Rose

(57) ABSTRACT

Long-acting injectable formulations are formed from a) a therapeutic agent selected from insecticides, acaricides, parasiticides, growth enhancers or oil-soluble NSAIDs, b) hydrogenated castor oil, and c) a hydrophobic carrier comprising i) triacetin, benzyl benzoate, ethyl oleate, or a combination thereof, and ii) acylated monoglycerides, propyl dicaprylates/dicaprates, caprylic/capric acid triglycerides or a combination thereof.

28 Claims, No Drawings

LONG ACTING INJECTABLE FORMULATIONS CONTAINING HYDROGENATED CASTER OIL

CROSS REFERENCE TO RELATED APPLICATIONS

Reference is made to provisional U.S. application Ser. No. 60/067,374, filed on Dec. 3, 1997. That application, as well as all documents cited herein and all documents cited in documents cited herein, are hereby incorporated by reference.

SUMMARY OF THE INVENTION

This invention is concerned with the unexpectedly long duration of activity which is observed when injectable formulations containing certain therapeutic agents are prepared using hydrogenated castor oil and a combination of hydrophobic or water immiscible carriers. Thus, it is an object of this invention to provide such a prolonged therapeutic effect. An additional object is to describe the therapeutic agents which may be employed in the long acting formulations. A still further object is to provide additional components which may be employed in the formulations. Additional objects will become apparent from a reading of the following description.

BACKGROUND OF THE INVENTION

The therapeutic agents which are used in the inventive formulations are well known to the practitioner to which this invention pertains. Classes of therapeutic agents contemplated by the inventive formulations include insecticides, acaricides, parasiticides, growth enhancers, and oil-soluble, nonsteroidal anti-inflammatory drugs (NSAIDS). Specific classes of compounds which fall within these classes include, for example, avermectins, milbemycins, nodulisporic acid and its derivatives, estrogens, progestins, androgens, substituted pyridylmethyl derivatives, phenylpyrazoles, and COX-2 inhibitors.

The avermectin and milbemycin series of compounds are potent anthelmintic and antiparasitic agents against a wide range of internal and external parasites. The compounds which belong to this series are either natural products or are semi-synthetic derivatives thereof. The structure of these two series of compounds are closely related and they both share a complex 16-membered macrocyclic lactone ring; however, the milbemycins do not contain the disaccharide substitutent in the 13-position of the lactone ring. The natural product avermectins are disclosed in U.S. Pat. No. 4,310,519 to Albers-Schonberg, et al., and the 22,23-dihydro avermectin compounds are disclosed in Chabala, et al., U.S. Pat. No. 4,199,569. For a general discussion of avermectins, which include a discussion of their uses in humans and animals, see "Ivermectin and Abamectin," W. C. Campbell, ed., Springer-Verlag, N.Y. (1989). Naturally occurring milbemycins are described in Aoki et al., U.S. Pat. No. 3,950,360 as well as in the various references cited in "The Merck Index" 12$^{th}$ ed., S. Budavari, Ed., Merck & Co., Inc. Whitehouse Station, N.J. (1996). Semisynthetic derivatives of these classes of compounds are well known in the art and are described, for example, in U.S. Pat. No. 5,077,308, U.S. Pat. No. 4,859,657, U.S. Pat. No. 4,963,582, U.S. Pat. No. 4,855,317, U.S. Pat. No. 4,871,719, U.S. Pat. No. 4,874,749, U.S. Pat. No. 4,427,663, U.S. Pat. No. 4,310,519, U.S. Pat. No. 4,199,569, U.S. Pat. No. 5,055,596, U.S. Pat. No. 4,973,711, U.S. Pat. No. 4,978,677, and U.S. Pat. No. 4,920,148.

European Patent Application 413,538 relates to an injectable formulation containing an avermectin compound and triacetin. European Patent Application 535,734 relates to an injectable formulation containing an avermectin compound and hydrogenated castor oil in a hydrophobic carrier such as triacetin. The formulations in both European Patent Applications are said to provide efficacy against external and internal parasites in animals only for up to 42 days. Neither of these applications suggests or teaches how to manipulate the composition of the formulation in order to achieve efficacy beyond 42 days.

Nodulisporic acid and its derivatives are a class of acaricidal, antiparasitic, insecticidal and anthelminitic agents known to a practitioner of the art. These compounds are used to treat or prevent infections in humans and animals. These compounds are described, for example, in U.S. Pat. No. 5,399,582 and WO 96/29073. Additionally, the compounds can be administered in combination with other insecticides, parasiticides, and acaricides. Such combinations include anthelminitic agents, such as those discussed above which include ivermectin, avermectin, and emamectin, as well as other agents such as thiabendazole, febantel or morantel; phenylpyrazoles such as fipronil; and insect growth regulators such as lufenuron. Such combinations are also contemplated in the present invention.

Generally, all classes of insecticides are provided for in this invention. One example of this class include substituted pyridylmethyl derivatives such as imidacloprid. Agents of this class are described, for example, in U.S. Pat. No. 4,742,060 or in EP 892,060. It would be well within the skill level of the practitioner to decide which individual compound can be used in the inventive formulation to treat a particular infection of an insect.

Phenylpyrazoles are another class of insecticides which possess excellent insecticidal activity against all insect pests including blood-sucking pests such as ticks, fleas etc., which are parasites on animals. This class of agents kills insects by acting on the gamma-butyric acid receptor of invertebrates. Such agents are described, for example, in U.S. Pat. No. 5,567,429, U.S. Pat. No. 5,122,530, and EP 295,117. It would be well within the skill level of the practitioner to decide which individual compounds can be used in the inventive formulations.

Insect growth regulators are another class of insecticides or acaricides, which are also provided for in the inventive formulations. Compounds belonging to this group are well known to the practitioner and represent a wide range of different chemical classes. These compounds all act by interfering with the development or growth of the insect pests. Insect growth regulators are described, for example, in U.S. Pat. No. 3,748,356; U.S. Pat. No. 3,818,047; U.S. Pat. No. 4,225,598; U.S. Pat. No. 4,798,837; and U.S. Pat. No. 4,751,225, as well as in EP 179,022 or U.K. 2,140,010. Again, it would be well within the skill level of the practitioner to decide which individual compounds can be used in the inventive formulation.

Estrogens, progestins, and androgens refers to classes of chemical compounds which are also well known to a practitioner in this art. In fact, estrogens and progestins are among the most widely prescribed drugs and are used, for example, alone or in combination for contraception or hormone replacement therapy in post menopausal women. Estrogens and progestins occur naturally or are prepared synthetically. This class of compounds also includes estrogens or progesterone receptor antagonists. Antiestrogens, such as tamoxifen and clomiphene, are used to treat breast cancer and infertility. Antiprogestives are used as contraceptives and anticancer drugs, as well as to induce labor or terminate a pregnancy.

The androgens and antiandrogens structurally related to the estrogens and progestins as they are also biosynthesized from cholesterol. These compounds are based on testosterone. Androgens are used for hypogonadism and promote muscle development. Antiandrogens are used, for example, in the management of hyperplasia and carcinoma of the prostate, acne, and male pattern baldness as well as in the inhibition of the sex drive in men who are sex offenders. Estrogen, progestins, and androgens are described, for example, in "Goodman & Gilman's The Pharmacological Basis of Therapeutics," $9^{th}$ ed., J. G. Handman and L. Elimbird, eds., Ch. 57 to 60, pp. 1411–1485, McGraw Hill, N.Y. (1996) or in "Principles of Medicinal Chemistry," $2^{nd}$ ed., W. O. Foye, ed., Ch. 21, pp. 495–559, Lea & Febiger, Philadelphia (1981).

Estrogens, progestins and androgens are also used in animal husbandry as growth promoters for food animals. It is known in the art that compounds of these classes act as growth-promoting steroids in animals such as cattle, sheep, pigs, fowl, rabbits, etc. Delivery systems to promote the growth of animals are described, for example, in U.S. Pat. No. 5,401,507, U.S. Pat. No. 5,288,469, U.S. Pat. No. 4,758,435, U.S. Pat. No. 4,686,092, U.S. Pat. No. 5,072,716 and U.S. Pat. No. 5,419,910.

NSAIDS are well known in the art. The classes of compounds which belong to this group include salicylic acid derivatives, para-aminophenol derivatives, indole and indene acetic acids, heteroaryl acetic acids, arylpropionic acids, anthranilic acids (fenamates), enolic acids, and alkanones. NSAIDS exert their activity by interfering with prostaglandin biosynthesis by irreversibly or reversibly inhibiting cycloxygenase. Also included are COX-2 inhibitors which act by inhibiting the COX-2 receptor. Compounds of this group possess analgesic, antipyretic and nonsteroidal anti-inflammatory properties. Compounds belonging to these classes are described, for example, in Chapter 27 of Goodman and Gilman on pages 617 to 658 or in Ch. 22 of Foye on pages 561 to 590 as well as in U.S. Pat. No. 3,896,145; U.S. Pat. No. 3,337,570; U.S. Pat. No. 3,904,682; U.S. Pat. No. 4,009,197; U.S. Pat. No. 4,223,299; and U.S. Pat. No. 2,562,830, as well as the specific agents listed in The Merck Index. This invention contemplates those compounds that are oil-soluble.

These and other embodiments are disclosed or are obvious from and encompassed by the following Detailed Description of the Invention.

DETAILED DESCRIPTION OF THE INVENTION

The present invention relates to a long acting injectable formulation for use in human and veterinary medicine, depending on the selected specific therapeutic agent and the indication being treated. The inventive formulation comprises:

(a) a therapeutic agent selected from the group consisting of, e.g., insecticides, acaricides, parasiticides, growth enhancers, and oil-soluble NSAIDS, (b) hydrogenated castor oil, and (c) a hydrophobic carrier comprising:
  (i) triacetin, benzyl benzoate, or ethyl oleate or a combination thereof,
  (ii) acylated monoglycerides, propyl dicaprylates/ dicaprates and caprylic acid/capric triglycerides.

More preferred, are long-acting injectable formulations wherein (a) a therapeutic agent selected from the group consisting of, e.g., avermectins, milbemycins, nodulisporic acid and its derivatives, estrogens, progestins, androgens, phenylpyrazoles and COX-2 inhibitors, (b) hydrogenated castor oil, and (c) a hydrophobic carrier comprising:
  (i) triacetin, benzyl benzoate, or ethyl oleate or a combination thereof,
  (ii) acetylated monoglycerides, propyl dicaprylates/ dicaprates, or caprylic/capric acid triglycerides or a combination thereof.

The formulations of the present invention considerably prolong the duration of activity. By the term "acyl" Applicants mean an organic acid group in which the OH of the carboxyl group is replaced by some other substituent; i.e., RCO wherein R is, for example a $C_1$–$C_{10}$–alkyl group or a carbocyclic aromatic or a heteroaromatic group. Examples of such groups include acetyl, propionyl, butyryl, isobutyryl, and benzoyl. The term "prolonged duration of activity" means that the activity of the therapeutic agent is extended beyond the time period normally achieved when the therapeutic agent is injected into a host using a conventional, prior art carrier. As conventional injectable formulations are well known in the art, a skilled practitioner could readily understand the meaning of this term. Generally, depending upon the agent, host, and disease state, activity can be prolonged for a period from up to 120 days to up to 180 days. Preferable time periods in which the duration of the agent is prolonged includes from 14 days to 180 days, 30 days to 150 days, 42 days to 120 days, and 60 days to 90 days. While not wishing to be bound by theory, it is believed this increase in activity is achieved because the inventive formulations significantly increase the plasma concentration in tissue for an extended period of time by up to about 2 weeks to about 24 weeks, with time periods of up to about 6, 8, 10, 12, 16 and 20 weeks being observed. With respect to avermectins and milbemycins, the present formulations have been found to have a considerably prolonged duration against internal and external parasites over prior injectable formulation of avermectins or milbemycins. In addition, the present formulations for avermectin and milbemycin provide significantly higher plasma levels at day 42 than prior long-acting formulations thereby producing efficacy for all relevant parasitic species.

Preferred long-acting injectable formulations comprise:

(a) about 1.0 to about 10.0% w/v of a therapeutic agent, (b) about 1 to about 3% w/v of hydrogenated castor oil, and (c) a hydrophobic carrier comprising:
  (i) about 30 to about 45% v/v of triacetin; benzyl benzoate or ethyl oleate; and
  (ii) about 55 to 70% of v/v of acetylated monoglycerides, propyl dicaprylates/dicaprates, or caprylic/capric triglycerides.

Even more preferred are the above formulations wherein about 1.0 to about 5.0% w/v of a therapeutic agent is present. Especially preferred are the inventive formulations wherein about 2.5 to about 5.0% w/v of a therapeutic agent is present.

Especially preferred long-acting formulation of the present invention comprises:

(a) an avermectin or milbemycin compound, (b) hydrogenated castor oil, and (c) triacetin and acetylated monoglycerides.

In an especially preferred embodiment, the long-acting formulation comprises:

(a) about 1.0 to about 5.0% w/v of an avermectin or milbemycin compound, (b) about 0.5 to about 3.5% w/v of hydrogenated castor oil, and (c) about 30 to about 45% v/v of triacetin and about 55 to about 70% v/v of acetylated monoglycerides.

In a most preferred embodiment, the long-acting formulation comprises:

(a) 3.15% w/v of ivermectin, (b) 1% w/v of hydrogenated castor oil, and
(c) 40% v/v of triacetin and up to 60% v/v of acetylated monoglycerides.

Another aspect of the invention is to provide a method for the prevention or treatment of parasite or insect infestations in a host in need thereof for an extended period of time by administering a single dose of a long-acting injectable formulation comprising the appropriate therapeutic agent. That duration typically, for example, lasts from up to about 1 month to about six months, depending upon the agent, host and indication being treated. Extensions of activity lasts from up to about 2 months to about 5 months and especially from up to 3 months to up to 4 months are observed. A further aspect of this invention is to promote the growth in animals by administering a single long-acting formulation according to the present invention wherein the therapeutic agent is an estrogen, progestin, or androgen. Another aspect of the present invention is a method to treat inflammation, pain or fever for an extended period of time in a host in need thereof by administering a single-dose of a formulation according to the present invention wherein the therapeutic agents are oil-soluble NSAIDS. An especially preferred aspect of the invention is to provide a method for the prevention or treatment of parasitic infestation in cattle for a minimum of 42 days which comprises administering to said cattle a single dose of a long-acting injectable formulation according to the present invention where the therapeutic agent is an avermectin or milbemycin.

Therapeutic agents used in the invention formulations include all known avermectins, milbemycins, nodulisporic acid and its derivatives, estrogens, progestins, androgens, oil-soluble NSAIDS, phenylpyrazoles, substituted pyridylmethyl compounds, and agents which act as insect growth regulators, which are compatible in the inventive formulations for their intended use. The ester and amide derivatives of these compounds, where applicable, as well as their salt forms are also contemplated. Specific compounds which belong to these classes of therapeutic agents are well known to the practitioner of this art. Likewise, the specific disease state as well as the particular dose would be well known to the practitioner.

Avermectins and milbemycins share the same common 16-membered macrocyclic lactone ring; however milbemycins do not possess the disaccharide substituent on the 13-position of the lactone ring.

While many avermectin compounds are known in the art, a representative structure of the class of compounds is as follows:

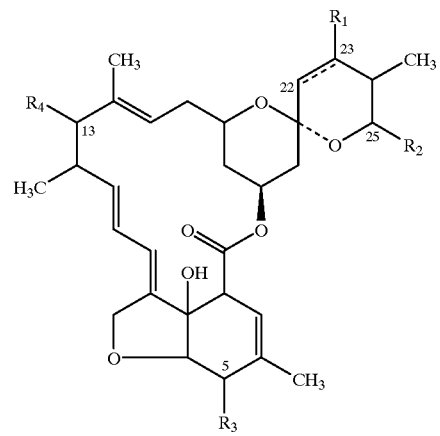

where the broken line indicates a single or a double bond at the 22,23-positions;

$R_1$ is hydrogen or hydroxy provided that $R_1$ is present only when the broken line indicates a single bond;

$R_2$ is alkyl of from 1 to 6 carbon atoms or alkenyl of from 3 to 6 carbon atoms or cycloalkyl of from 3 to 8 carbon atoms;

$R_3$ is hydroxy, methoxy or $=NOR_5$ where $R_5$ is hydrogen or lower alkyl; and $R_4$ is hydrogen, hydroxy or

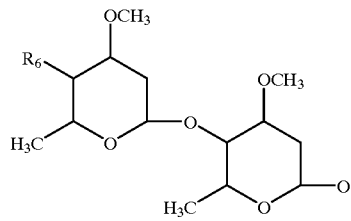

where $R_6$ is hydroxy, amino, mono-or di-lower alkylamino or lower alkanoylamino.

The preferred compounds are avermectin B1a/B1b (abamectin), 22,23-dihydro avermectin B1a/B1b (ivermectin) and the 4"-acetylamino-5-ketoximino derivative of avermectin B1a/B1b. Both abamectin and ivermectin are approved as broad spectrum antiparasitic agents. The structures of abamectin and ivermectin are as follows:

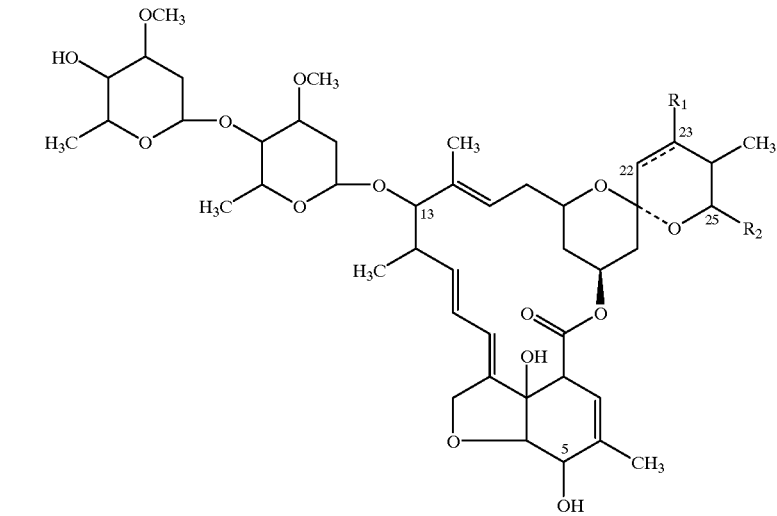

wherein for abamectin the broken line represents a double bond and $R_1$ is not present and for ivermectin the double bond represents a single bond and $R_1$ is hydrogen; and $R_2$ is isopropyl or sec-butyl.

The 4"-acetylamino-5-ketoximino derivatives of avermectin B1a/B1b has the following structural formula:

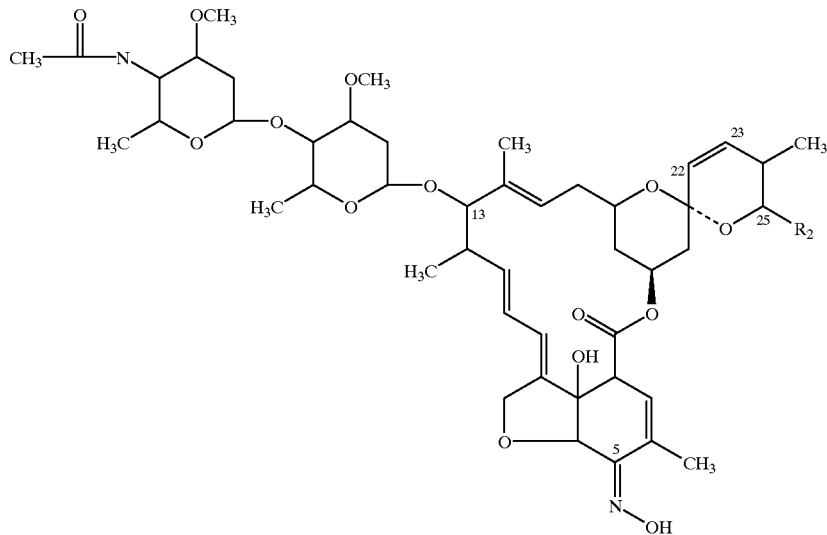

where $R_2$ is isopropyl or sec-butyl.

The avermectin products are generally prepared as a mixture of at least 80% of the compound where $R_2$ is sec-butyl and no more than 20% of the compound where $R_2$ is isopropyl. Other preferred avermectins, include ememectin, epinomectin and doramectin. Doramectin is disclosed in U.S. Pat. No. 5,089,490 and EP 214738. This compound has the following structure:

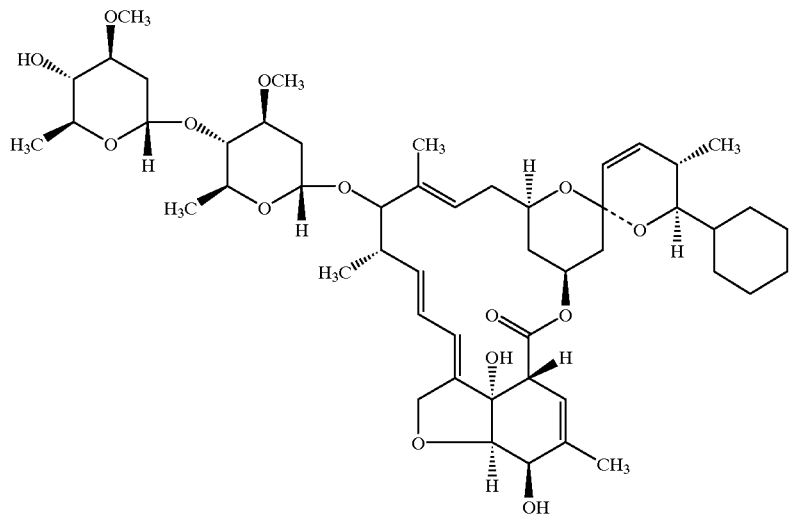

In the present formulations, ivermectin is especially preferred. A representative structure for a milbemycin is that for milbemycin $\alpha_1$:

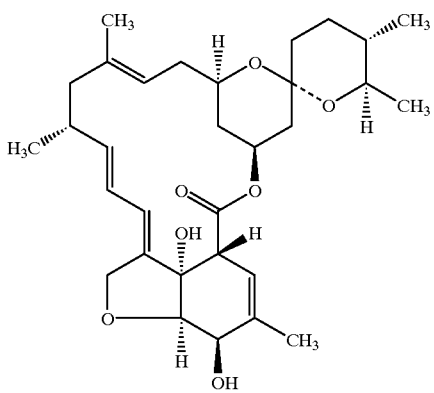

An especially preferred milbemycin is moxidectin, whose structure is as follows:

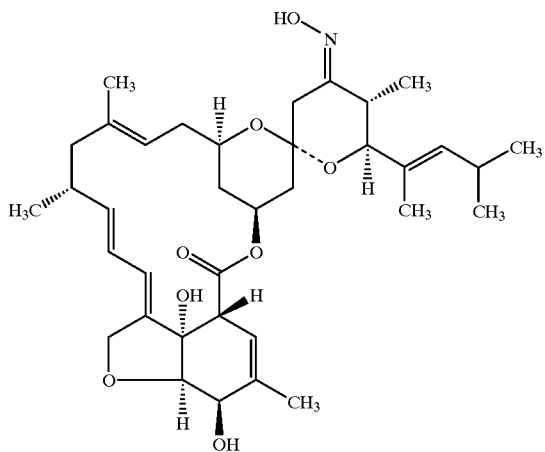

The compound is disclosed in U.S. Pat. No. 5,089,490.

Insecticides contemplated by this invention are also well known in the art and such compounds include substituted pyridylmethyl derivatives and phenylpyrazoles. An especially preferred substituted pyridylmethyl derivative is imidacloprid. An especially preferred phenylpyrazole is fipronil, whose chemical name is 5-amino-3-cyano-1-(2,6-dichloro-4-trifluoromethylphenyl)-4-trifluoromethylpyrazole. Fipronil is well known in the art as a flea and tick agent. Additional insecticides included by the invention include insect growth regulators. Especially preferred insect growth regulators include diflubenzuron, lufenuron, methoprene, phenoxycarb, pyriproxyfen, and cyromazine.

Specific estrogen, progestin and androgen compounds are well known to the practitioner. Especially preferred compounds belonging to this class include progesterone, estradiol benzoate and trenbolone acetate.

Oil-soluble NSAIDS are also well known to the practitioner. Classes of NSAIDS which are preferred are indole and indecene acetic acids and heteroaryl acetic acids. Especially preferred compounds include indomethacin, ketorolac, caprofen, flunixin, ketoprofen, meloxicam, naproxen, and phenylbutazone.

Hydrogenated castor oil is refined, hydrogenated, and deodorized castor oil, consisting mainly of the triglyceride of hydroxystearic acid. The hydrogenated castor oil is readily prepared using normal techniques known to those skilled in the art of preparing hydrogenated castor oils and one suitable form of hydrogenated castor oil is available commercially under the trade name "Thixcin R" from NL Industries. While not wishing to be bound by theory, it appears that hydrogenated castor oil, being a waxy hydrophobic solid, is left at the injection site entrapping the therapeutic agent after the hydrophobic carrier has diffused from the injection site; it is this hydrophobic hydrogenated castor oil/therapeutic agent matrix that forms a "depot" of the active material which slowly diffuses from the injection site over a prolonged period of time. The hydrogenated castor oil constitutes approximately 1% w/v of the present formulation.

The hydrophobic carrier of the present formulation comprises a mixture of
  (i) triacetin, benzylbenzoate, ethyl oleate or a combination thereof; and
  (ii) acylated monoglycerides, propyl dicaprylates/dicaprates, or caprylic/capric triglycerides or a combination thereof.

These compounds as well as their sources are well known in the art. For example, triacetin (glyceryl triacetate or glycerol triacetate) and acetylated monoglycerides (available under the tradename "Myvacet 9-45" from Quest International). The ratio of component (i) to component (ii) used in the present formulation is generally from 45:55 to 30:70; preferably the ratio is approximately 40:60. In addition to the hydrogenated castor oil, the therapeutic agent and the hydrophobic carrier, the formulation can contain other inert ingredients such as antioxidants or preservatives. Antioxidant such as a propyl gallate, BHA (butylated hydroxy anisole), BHT (butylated hydroxy toluene) monothioglycerol and the like may be added to the present formulation. The antioxidants are generally added to the formulation in amounts of from about 0.01 to about 2.0% (w/v). Preservatives such as the parabens (methylparaben and/or propylparaben) are suitably used in the formulation in amounts ranging from about 0.01 to about 2.0 w/v.

The long-acting injectable formulation of the present invention may be prepared by adding a dispersion of hydrogenated castor oil in acetylated monoglycerides, propyl dicaprylates/dicaprates or caprylic/capric triglycerides to a solution comprising the therapeutic agent, and any other inert ingredients, in triacetin benzyl benzoate or ethyl oleate, and mixing the liquids until uniform. Since the long acting formulation is intended for injection, it is necessary that it be sterilized. Heat sterilization is generally to be avoided in the situation where avermectin or milbemycin compounds are used since these compounds are unstable at autoclave temperatures. Rather, membrane sterilization is preferred in those situations with dissolved solids and gamma sterilization for the hydrogenated castor oil. The sterile hydrogenated castor oil is dispersed in the product aseptically and then aseptically packaged.

The instant formulation is equally applicable to other compounds used for injection as long as such compounds are soluble in the mixture of the hydrogenated castor oil and hydrophobic carrier. Additional compounds that can be used in this formulation are other antiparasitic agents and antibiotics, therapeutic vitamin and mineral supplements, and other agents that are assisted in their therapeutic effect by having their effects extended over a prolonged period of time. Again, such compounds would be well known to the practitioner.

The instant long-acting formulations are administered to a warm-blooded animals such as humans, cattle, sheep, pigs, cats, dogs, horses, and the like by intramuscular or subcutaneous injection. The amount of therapeutic agent depends on the individual therapeutic agent, the animal being treated, the disease state, and the severity of the disease state. The determination of those factors is well within the skill level of the practitioner. Generally, such preparation normally contain about 0.0005 to about 50% w/v of therapeutic agent. Preferred formulations are those containing about 0.01 to 10% w/v of therapeutic agent and especially preferred formulations are those containing about 2.5 to about 5% w/v of therapeutic agent. For the avermectins and milbemycins, the formulations will generally be prepared to administer from about 0.1 to about 2 mg/kg, preferably from about 0.4 to about 0.85 mg/kg and most preferably from about 0.6 to about 0.7 mg/kg of the active ingredient. At a preferred dose volume of about 1 ml to treat 50 kg of animal body weight the formulation contains from about 5 to about 50 mg of the active agent per ml of solution or about 0.5 to about 10%, w/v preferably about 2.5 to about 5% w/v. However, depending upon the activity of the compound and the animal being treated, doses as low as about 0.3% w/v of the active ingredient are usable. For nodulisporic acid and its derivatives, a formulation containing about 0.0005 to about 5% w/v of the active compound is preferred.

The present formulation provides for an extended period of treatment. For avermectins and milbemycins a minimum of 42 days of activity against endo- and ectoparasites is obtained without causing tissue irritation. The extended period of time for the other therapeutic agents is readily determined by one skilled in the art and is determined by such factors as the therapeutic agent, disease state, host and severity of the infection. While the previously reported avermectin formulation containing hydrogenated castor oil in triacetin did produce prolonged plasma level compared to a formulation without hydrogenated castor oil, it did not achieve a plasma level efficacious against all relevant parasitic species at the 42 day target. In contrast the present formulation using avermectins or milbemycins surprisingly provides a significantly higher plasma at day 42 and beyond. The present formulation is also efficacious against ticks and Dermatobia hominis for up to 75 and 140 days, respectively.

The following example is provided in order that the invention might be more fully understood. It is not to be construed as a limitation of the invention.

EXAMPLE 1

| Material | % | Amount |
|---|---|---|
| Ivermectin | 3.15% w/w | 17.6 gm |
| n-propyl gallate | 0.02% w/w | 0.10 gm |
| Thixcin R | 1.0% w/w | 5.0 gm |
| triacetin | 40.0% w/w | 200.0 gm |
| Myvacet 9-45 | qs 100% w/w | qs to 500.0 gm |

Triacetin was added to n-propyl gallate and ivermectin in an Erlenmyer flask and mixed until all of the n-propyl gallate dissolved. Myvacet 9-45 was placed in a non-glass beaker in a 50° C. water bath, and mixed at a low speed with a dispersator mixer until the temperature of the content reached 50° C. Thixcin R was then added slowly to the vortex of the mixing Myvacet 9-45. When all the Thixcin R was added, the speed of the mixer was slowly increased to 60 rpm and mixing continued for 20 minutes. The beaker was removed from the water bath and allowed to cool to 30° C., while mixing continued at about 25 rpm. The triacetin solution was added to the Thixcin R/Myvacet 9-45 mixture and the liquids were mixed until uniform.

EXAMPLE 2

| Material | % | Amount/2000 L. |
|---|---|---|
| Ivermectin | 3.15% w/w | 63.0 kg |
| triacetin | 40.0% v/v | 800.0 L |
| hydrogenated castor oil | 1.0% w/w | 20.0 kg |
| BHT | 0.02% w/v | 0.4 kg |
| methylparaben | 0.18% w/v | 3.6 kg |
| propylparaben | 0.02% w/v | 0.4 kg |
| Myvacet 9-45 | qs 100% v/v | qs to 1200.0 L |

Ivermectin, BHT, methyl and propyl paraben were dissolved in 800 L of triacetin, and the solution was sterile filtered into a 2000 L tank equipped with an agitator. Myvacet 9-45 was sterile filtered into a 150 L tank capable of maintaining a batch temperature of 60° C. and equipped with an agitator and with an aseptic addition of sterile powder capability. The gamma sterilized hydrogenated castor oil was dispersed in the Myvacet 9-45, and the dispersion was heated to 50° C., then transferred to the triacetin solution through a microfluidizer. The liquids were mixed until uniform and then aseptically packaged in low density polyethylene containers.

EXAMPLE 3

The plasma levels of ivermectin administered once subcutaneously at a dose of 630 mcg/kg bodyweight were determined in cattle for two formulations: formulation I contains ivermectin 3.15%, n-propyl gallate 0.02%, Thixcin R 1.5% and triacetin qs to 100%; formulation II has the composition given in Example 2. Ten animals were used for formulation I and six were used for formulation II. Mean plasma levels (ng/ml) are shown in the following Table:

| | Days post dosing | | | | | |
|---|---|---|---|---|---|---|
| Formulation | 3 | 14 | 21 | 28 | 35 | 42 |
| I | 80 | 18 | 10 | 6 | 4 | 2 |
| II | 21 | 25 | 22 | 16 | 13 | 9 |

The mean plasma level for formulation II was greater than 3 ng/ml on day 70.

The 42-day plasma level of formulation I (2 ng/ml) is not sufficient to produce efficacy against Cooperia onocophora and Nematodirus which require an ivermectin plasma level of 3 to 4 ng/ml.

EXAMPLE 4

To facilitate the manufacture of large scale batches the following process was developed which results in a product that meets the same release specifications as the product manufactured in Example 2. The formula is also the same as used in Example 2. Ivermectin, BHT, methyl and propyl paraben are dissolved a mixture of the triacetin and Myvacet 9-45. The solution is sterile filtered. The gamma sterilized hydrogenated castor is aseptically dispersed in sterile solution using an in-line educator/homogenizer system. Such in-line system can be a Flashblend system. The product is heated and recirculated through the system until the product temperature is from 42 to 50° C. Then the product is aseptically packaged.

Having thus described in detail preferred embodiments of the present invention, it is to be understood that the invention defined by the appended claims is not to be limited by particular details set forth in the above description as many apparent variations thereof are possible without departing from the spirit or scope thereof.

What is claimed is:

1. A long-acting injectable formulation comprising:
   (a) a therapeutic agent selected from the group consisting of insecticides, acaricides, parasiticides, growth enhancers and oil-soluble NASIDS,
   (b) hydrogenated castor oil, and
   (c) a hydrophobic carrier comprising:
      (i) triacetin, benzyl benzoate or ethyl oleate or a combination thereof; and
      (ii) acylated monoglycerides, propyl dicaprylates/dicaprates, caprylic/capric acid triglycerides, or a combination thereof.

2. A long-acting injectable formulation comprising:
   (a) a therapeutic agent selected from the group consisting of avermectins, milbemycins, nodulisporic acid and its derivatives, estrogens, progestins, androgens, substituted pyridylmethyl derivatives, phenylpyrazoles, and COX-2 inhibitors,
   (b) hydrogenated castor oil, and
   (c) a hydrophobic carrier comprising:
      (i) triacetin, benzyl benzoate or ethyl oleate or a combination thereof; and
      (ii) acetylated monoglycerides, propyl dicaprylates/dicaprates, caprylic/capric triglycerides, or a combination thereof.

3. The long-acting injectable formulation according to claim 1 comprising
   (a) about 1.0 to about 10.0 w/v of a therapeutic agent;
   (b) about 0.3 to about 5% w/v of hydrogenated castor oil;
   (c) a hydrophobic carrier comprising:
      (i) about 30 to about 45% v/v of triacetin; benzylbenzoate or ethyloleate; and
      (ii) about 55 to 70% of v/v of acetylated monoglycerides, propyl dicaprylates/dicaprates, or caprylic/capric triglycerides.

4. The long-acting injectable formulation according to claim 2 comprising
   (a) about 1.0 to about 10.0 w/v of a therapeutic agent;
   (b) about 0.3 to about 5% w/v of hydrogenated castor oil;
   (c) a hydrophobic carrier comprising:
      (i) about 30 to about 45% v/v of triacetin; benzyl benzoate or ethyl oleate; and
      (ii) about 55 to 70% of v/v of acetylated monoglycerides, propyl dicaprylates/dicaprates, or caprylic/capric triglycerides.

5. The long-acting injectable formulation according to claim 2 wherein about 2.5 to about 5.0% w/v of a therapeutic agent is present.

6. The long-acting injectable formulation according to claim 2 wherein the therapeutic agent is an avermectin or a milbemycin.

7. The long-acting injectable formulation according to claim 6, wherein the avermectin is ivermectin, abamectin, ememectin, eprinomectin, or doramectin and the milbemycin is moxidectin.

8. The long-acting injectable formulation according to claim 2, wherein the therapeutic agent is an estrogen, progestin or androgen.

9. The long-acting injectable formulation according to claim 8, where the estrogen, progestin or androgen is estradiol benzoate, progesterone, or trenbolone acetate.

10. The long-acting injectable formulation according to claim 2, wherein the therapeutic agent is nodulisporic acid or its derivatives.

11. The long-acting injectable formulation according to claim 2, wherein the therapeutic agent is a substituted pyridylmethyl derivative or a phenylpyrazole.

12. The long-acting injectable formulation according to claim 11, wherein the therapeutic agent is imidacloprid or fipronil.

13. The long-acting injectable formulation according to claim 2, wherein the therapeutic agent is a COX-2 inhibitor.

14. The long-acting injectable formulation according to claim 1, wherein the therapeutic agent is an oil-soluble, nonsteroidal anti-inflammatory drug.

15. The long-acting injectable formulation according to claim 14, wherein the therapeutic agent is carprofen, flunixin, ketoprofen, meloxicam, naproxen or phenylbutazone.

16. The long-acting injectable formulation according to claim 1, wherein the therapeutic agent is an insect growth regulator.

17. The long-acting injectable formulation according to claim 16, wherein the therapeutic agent is diflubenzuron, lufenuron, methoprene, phenoxycarb, pyriproxyfen, and cyromazine.

18. The long-acting injectable formulation according to claim 1, which further comprises an antioxidant or a preservative.

19. The long-acting injectable formulation according to claim 2 where about 1 to about 3.0% w/v of hydrogenated caster oil is present and hydrophobic carrier comprises about 40% v/v of triacetin, benzlybenzoate or ethyloleate and about 60% v/v of acetylated monoglycerides, propyl dicaprylates/dicaprates, or caprylic/capric triglycerides.

20. The long-acting injectable formulation of claim 2 which comprises:
   (a) about 1.0 to about 5.0% w/v of an avermectin compound,
   (b) about 1 to about 3% w/v of hydrogenated castor oil, and
   (c) about 30 to about 45% v/v of triacetin and 55 to 70% v/v of acetylated monoglycerides.

21. The long-acting injectable formulation of claim 2 which comprises:
   (a) about 3.15% w/v of ivermectin,
   (b) about 1% w/v of hydrogenated castor oil, and
   (c) about 40% of triacetin and up to about 60% v/v of acetylated monoglycerides.

22. The long-acting injectable formulation of claim 2 which further comprises an antioxidant.

23. The long acting injectable formulation of claim 2 which further comprises a preservative.

24. The long acting injectable formulation of claim 22 wherein said antioxidant is selected from n-propyl gallate, BHA, BHT and monothioglycerol.

25. The long-acting injectable formulation of claim 23 wherein said preservative is selected from the parabens.

26. The long-acting injectable formulation of claim 21 which further comprises an antioxidant selected from n-propyl gallate, BHA, BHT and monothioglycerol.

27. The long-acting injectable formulation of claim 26 which further comprises a preservatives selected from the parabens.

28. The long acting injectable formulation of claim 21 which further comprises BHT and one or more preservatives from the parabens.

* * * * *